United States Patent [19]

Damanj

[11] Patent Number: 5,242,910
[45] Date of Patent: Sep. 7, 1993

[54] SUSTAINED RELEASE COMPOSITIONS FOR TREATING PERIODONTAL DISEASE

[75] Inventor: Nalinkant C. Damanj, Cincinnati, Ohio

[73] Assignee: The Procter & Gamble Company, Cincinnati, Ohio

[21] Appl. No.: 960,614

[22] Filed: Oct. 13, 1992

[51] Int. Cl.$^5$ ............ A61K 9/06; A61K 31/65; A61K 31/74

[52] U.S. Cl. .................. 514/152; 514/772.3; 514/772.6; 514/900; 514/902; 514/944; 514/953; 514/969

[58] Field of Search ............ 514/152, 900, 902, 772.3, 514/772.6, 953, 969

[56] References Cited

U.S. PATENT DOCUMENTS

| | | | |
|---|---|---|---|
| 3,498,957 | 3/1970 | Jacobson | 260/78.3 |
| 3,636,956 | 1/1972 | Schneider | 128/335.5 |
| 3,736,646 | 6/1973 | Schmitt et al. | 29/458 |
| 3,867,190 | 2/1975 | Schmitt et al. | 117/138.8 |
| 3,978,203 | 8/1976 | Wise | 514/772.6 |
| 4,017,615 | 4/1977 | Shasta et al. | 424/241 |
| 4,137,921 | 2/1979 | Okuzumi et al. | 128/335.5 |
| 4,191,747 | 3/1980 | Scheicher | 424/94 |
| 4,328,204 | 5/1982 | Wasserman et al. | 424/78 |
| 4,443,430 | 4/1984 | Mattei et al. | 424/78 |
| 4,454,110 | 6/1984 | Caslavsk et al. | 424/54 |
| 4,474,750 | 10/1984 | Gaffar et al. | 424/49 |
| 4,568,536 | 2/1986 | Kronenthal et al. | 424/22 |
| 4,569,837 | 2/1986 | Suzuki et al. | 424/28 |
| 4,624,256 | 11/1986 | Messier et al. | 128/335.5 |
| 4,650,665 | 3/1987 | Kronenthal et al. | 424/435 |
| 4,652,441 | 3/1987 | Okada et al. | 424/19 |
| 4,670,252 | 6/1987 | Sampathkumar | 424/53 |
| 4,685,883 | 8/1987 | Jernberg | 433/215 |
| 4,692,328 | 9/1987 | Kitchell et al. | 514/772.3 |
| 4,711,782 | 12/1987 | Okada et al. | 424/455 |
| 4,713,243 | 12/1987 | Sheraldi et al. | 424/151 |
| 4,764,377 | 8/1988 | Goodson | 424/435 |
| 4,772,484 | 9/1988 | Kitchell et al. | 427/2 |
| 4,780,320 | 10/1988 | Baker | 424/493 |
| 4,789,662 | 12/1988 | Thomas-Leurquin et al. | 514/21 |
| 4,810,775 | 3/1989 | Bendix et al. | 528/480 |
| 4,900,552 | 2/1990 | Sanvordeker et al. | 424/422 |
| 4,920,203 | 4/1990 | Tang et al. | 525/409 |
| 4,933,182 | 6/1990 | Higashi et al. | 424/435 |
| 4,969,884 | 11/1990 | Yum | 604/892.1 |
| 5,030,216 | 7/1991 | Theeuwes et al. | 604/892.1 |
| 5,061,281 | 10/1991 | Mares et al. | 623/11 |
| 5,084,267 | 1/1992 | Damani | 424/426 |
| 5,198,220 | 3/1993 | Damani | 514/772.6 |
| 5,200,195 | 4/1993 | Done et al. | 424/473 |

FOREIGN PATENT DOCUMENTS

| | | |
|---|---|---|
| 0140766 | 5/1985 | European Pat. Off. . |
| 0241179 | 10/1987 | European Pat. Off. . |
| 0297535 | 1/1989 | European Pat. Off. . |
| 3635679 | 5/1988 | Fed. Rep. of Germany . |
| 63-79817 | 4/1988 | Japan . |
| 63-287719 | 11/1988 | Japan . |

Primary Examiner—Shep K. Rose
Attorney, Agent, or Firm—J. D. Schaeffer; D. C. Mohl; K. W. Zerby

[57] ABSTRACT

This invention relates to compositions/devices and methods for treating diseases of the oral cavity in humans and lower animals using polylactide/glycolide compositions/devices also containing triacetin for releasing drugs in the oral cavity.

5 Claims, No Drawings

SUSTAINED RELEASE COMPOSITIONS FOR TREATING PERIODONTAL DISEASE

TECHNICAL FIELD

This invention relates to compositions/devices for treating diseases of the oral cavity which compositions/devices are placed in or around the periodontal pocket. The invention also relates to methods of using the compositions/devices in humans and lower animals suffering from such diseases.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Recent developments in the art are directed toward delivering the therapeutic agent directly to the periodontal pocket, in some cases in a controlled release formulation. Goodson et al. have described the use of a drug-filled polymer hollow fiber. [J. M. Goodson et al., "Periodontal Therapy by Local Delivery of Tetracycline", *J. Clin. Periodontal.* 6, 83 (1979), J. Lindhe et al., "Local Tetracycline Delivery Using Hollow Fiber Devices in Periodontal Therapy", *J. Clin. Periodontal.* 6, 141 (1979) and R. L. Dunn et al., "Monolithic Fibers for Controlled Delivery of Tetracycline", in *Proc. Ninth Int. Symposium on Controlled Release of Bioactive Materials,* Ft. Lauderdale, Fla., July (1982)]. This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman [J. Coventry and H. N Newman, "Experimental Use of a Slow Release Device Employing Chlorhexidine Gluconate in Areas of Acute Periodontal Inflammation", *J. Clin. Periodontal.* 9, 129 (1982)] and Addy et al. [M. Addy et al., "The Development and in vitro Evaluation of Acrylic Strips and Dialysis Tubing for Local Drug Delivery", *J. Periodontal* 53, 693 (1982)] using acrylic strips 1 mm or more long, impregnated with chlorhexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569,837.

In addition to the above approaches, the prior art also discloses using putty-like compositions containing an antimicrobial for insertion into the periodontal pocket. A material disclosed as suitable is a copolymer of lactide and glycolide. See U.S. Pat. No. 4,650,665, Mar. 17, 1987 to Kronenthal et al., incorporated herein by reference.

The present inventor has discovered that lactide and glycolide copolymers have limited pliability and solubility in terms of processing which are favorably improved by combining the copolymers with triacetin.

It is therefore an object of the present invention to provide lactide/glycolide compositions/devices containing triacetin suitable for treating diseases of the oral cavity overcoming such problems.

It is a further object of the present invention to provide such compositions/devices using copolymers of lactide and glycolide combined with triacetin.

It is still a further object of the present invention to provide a method of treating periodontal disease.

All percentages and ratios used in here are by weight unless otherwise indicated.

All measurements are made at 25° C. unless indicated.

SUMMARY OF INVENTION

The present invention relates to compositions/devices and methods for treating diseases of the oral cavity by inserting the compositions/devices into the periodontal pocket or around said pocket of humans and/or lower animals. The compositions/devices comprise copolymers of lactide and glycolide, triacetin (as a solvent/plasticizer) and an agent providing relief of oral cavity diseases.

DETAILED DESCRIPTION OF THE INVENTION

The essential as well as optional components of the compositions/devices of this invention are described below.

Lactide/Glycolide Copolymers

The copolymers of the present invention contain mixtures of lactide and glycolide monomers. Lactide monomeric species preferably comprise 15% to about 85%, most preferably from about 35% to about 65% of the polymers, while glycolide monomers comprise from about 15% to about 85% of the polymer, preferably from about 35% to about 65% on a molar basis. The molecular weight of the copolymer lies in the range of from about 1000 to about 120,000 (number average). These polymers are described in detail in U.S. Pat. No. 4,443,430, Apr. 17, 1984, to Mattei incorporated herein by reference.

The polymer generally comprises from about 1% to about 90%, preferably from about 10% to about 70% of the compositions/devices of the present invention. Less polymer is necessary as the amount of lactide goes up.

Triacetin

The second essential component of the present invention is triacetin. Triacetin, known chemically as 1,2,3-propanetriol triacetate or glyceryl triacetate, is a commercially available material and is prepared by the acetylation of glycerol. The unique feature of this invention is that triacetin is a material that is non-toxic and safe for use in the human body which may function as a solubilizer and/or stabilizer in the composition.

Triacetin may act as a solvent for the lactide/glycolide copolymers which does not degrade the polymers. Triacetin, in addition, may act as a stabilizer for the polymers and/or drug active used in the invention thereby increasing the shelf life of the composition. Triacetin also has antifungal activity, which may enhance the treatment of a fungal infection in the presence of other antimicrobial or antibiotic therapies.

Triacetin is used in the present compositions/devices at a level of from about 1% to about 90%, preferably from about 1% to about 70%, most preferably from about 3% to about 50%. The higher levels of triacetin, such as from about 20% to about 90%, are used when it is desired that the compositions be in gel or liquid form rather than in solid form. Gel form of the present invention compositions is most preferred, and typically comprise from about 25% to about 50% triacetin.

Drug Active

The drugs useful for use in the present compositions/devices are varied and many and include any agent which provides treatment or prevention management of diseases of the oral cavity. Some therapeutic agents which are amenable to delivery by this means and are potentially of value for periodontal therapy, include (but are not limited to) antibacterial agents such as iodine, sulfonamides, mercurials, bisbiguanides, or phenolics; antibiotics such as tetracycline, neomycin, kanamycin, metronidazole, or clindamycin; anti-inflammatory agents such as aspirin, naproxen, ibuprofen, flurbiprofen, indomethacin, eugenol, or hydrocortisone; immune-suppressive or stimulatory agents such as methotrexate or levamasole; dentinal desensitizing agents such as strontium chloride or sodium fluoride; odor masking agents such as peppermint oil or chlorphyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an anti-inflammatory agent may be combined in a single delivery system to provide combined effectiveness.

The drug active is used at a level of from about 1% to about 90%, preferably from about 5% to about 75%, most preferably from about 10% to about 50% of the compositions/devices. The compositions/devices, for example, are designed to release drug to provide steady state number average concentrations of from about 10 μg to about 2000 μg, preferably from about 50 μg to about 1500 μg, most preferably from about 100 μg to about 1000 μg per milliliter of the gingival crevicular fluid of a treated periodontal pocket.

The steady state release rates can be altered by varying component ratios of the compositions. The steady state conditions are preferably used since initial bursts are accounted for as well as delays in release. For example, in the case of a ten (10) day therapy, steady state is generally reached in about one to three days.

Optional Components

In addition to the drug active, the compositions/devices of the present invention may include a variety of optional components. Such components include, but are not limited to, surfactants, flavoring agents, viscosity controlling agents, complexing agents, antioxidants, other polymers such as carboxymethyl cellulose, gums such as guar gum, waxes/oils such as castor wax, castor oil, glycerol, dibutyl phthalate and di(2-ethylhexyl) phthalate, coloring agents as well as many others. If used, these optional components comprise from about 0.1% to about 20%, preferably from about 0.5% to about 5% of the total composition/device.

METHOD OF MANUFACTURE

Method of manufacturing the compositions/devices of this invention are disclosed in the Examples.

The following Examples further describe and demonstrate the preferred embodiments within the scope of the present invention. The Examples are given solely for the purpose of illustration and are not to be construed as limitations of the present invention as many variations thereof are possible without departing from it spirit and scope.

EXAMPLE I

The following is an exemplary composition/device of the present invention.

|  | Wt. % |
| --- | --- |
| Tetracycline hydrochloride | 50 |
| Poly(lactyl-co-glycolide)/50:50 copolymer | 45 |
| Triacetin | 5 |

The above composition can be prepared in a number of different ways. One way is as follows: Polymer is charged into a 80° C., electrically heated mixer, equipped with high shear Sigma type rotor blades. Triacetin is added and mixed into the polymer. The drug is added and mixed until uniform. The drug polymer blend is removed for further processing into desired size and shape devices.

The compositions/devices of this invention are inserted into the periodontal pocket or gingival region, and may be administered in the form of a particle, film or sheet. The size, shape, and thickness are not particularly critical and can be changed according to the condition of the disease to be treated. Ordinarily, the size, shape, and thickness are changed according to the size of the periodontal pocket of the patient or the condition of the gingiva. The devices may be for example of a size such that the thickness is in the range of 0.01 to 2 mm, preferably from about 0.1 to about 1 mm; the width in the range of 0.1 to about 5 mm, preferably from about 0.1 to about 4 mm; and the length in the range of from about 1 to about 15 mm, preferably from about 3 to about 10 mm.

If in the above example, the triacetin level is increased to about 40%, the composition is in the form of a fluid viscous gel which may be put into the periodontal pocket using a syringe-like apparatus.

EXAMPLE II

Given below is another composition/device of the present invention:

|  | Wt. % |
| --- | --- |
| Chlorhexidine base | 20 |
| Poly(lactide-co-glycolide) 50:50 copolymer | 70 |
| Triacetin | 10 |

EXAMPLE III

Given below is still another composition/device representative of the present invention:

|  | Wt. % |
| --- | --- |
| Clindamycin phosphate | 20 |
| Poly(lactide-co-glycolide) 65:35 copolymer | 60 |
| Carboxymethyl cellulose sodium | 15 |
| Triacetin | 5 |

While solid phase devices of the compositions illustrated above are very useful and convenient for most treatments, there may also be a need for fluid compositions that can be inserted into the periodontal cavities via syringe using either a needle or a catheter. Examples of such instances include difficult to reach areas where the periodontal cavities are irregular, narrow and very deep or those involving furcations. For this reason, fluid viscous gel or paste compositions are developed based on the above mentioned principles of compounding the poly(lactyl-co-glycolide) polymers as illustrated in the following:

Fluid viscous gel compositions using triacetin as carrier solvent with or without propylene and/or polyethylene glycol for poly(lactyl-co-glycolide) polymer may be prepared. Representative examples of such sustained release compositions are as follows:

EXAMPLE IV

|  | Wt. % |
| --- | --- |
| Tetracycline hydrochloride | 35 |
| Poly(lactyl-co-glycolide) | 25 |
| Triacetin | 40 |

EXAMPLE V

|  | Wt. % |
| --- | --- |
| Tetracycline Base | 27 |
| Poly(lactyl-co-glycolide) | 24 |
| Triacetin | 40 |
| Polyethylene glycol 400 | 9 |

EXAMPLE VI

|  | Wt. % |
| --- | --- |
| Chlorhexidine diacetate | 30 |
| Poly(lactyl-co-glycolide)/50:50 copolymer | 30 |
| Triacetin | 40 |

Compositions corresponding to the above Examples can be prepared by a variety of pharmaceutical or cosmetic procedures. For example, composition of Example IV can be prepared by first dissolving the copolymer into the triacetin using a propeller mixer. Micronized drug is slowly added and mixed into the polymeric solution to a uniform consistency. Such compositions are gel-like fluids which can be inserted into the diseased periodontal cavities via syringe.

A surprising feature of such fluid viscous gel or paste-like compositions is their transformation into near solid phase in the presence of aqueous fluid such as water, aqueous buffers or crevicular fluid. For example, when a sample of such a gel is placed into a tube containing water of human serum, the composition becomes nearly solid in the receptor phase. This is believed to be due to insolubility of the poly(lactyl-co-glycolide) copolymer in water, and related aqueous solvents such as may be present in crevicular fluid. Thus, even though such fluid compositions can be used advantageously when desired from a syringe-like apparatus, they still offer the uncompromised advantages of solid devices at the treatment sites. Further, since such polymeric materials do undergo slow degradation via hydrolysis, the drug continues to release in a sustained manner from such compositions.

An additional surprising feature of such gel or paste-like compositions is the unique benefit that triacetin provides when added to the compositions. Triacetin acts as a solvent for the poly(lactyl-co-glycolide) copolymer, and does not degrade the copolymer. Triacetin, in addition, acts as a stabilizer for the copolymer and antimicrobial agent, thereby increasing the shelf life of the composition.

For the purpose of experimental evaluation, stainless steel wire loops are fabricated to provide 0.5 cm. internal diameter. Loops are filled with test compositions, and the test samples are lowered into vials filled with pH 7.4 phosphate buffers. In contact with the fluid receptor, a gel of the present invention is transformed into more viscous material in about a minute. Initially, the drug is released to provide a burst during the phase transition stage to supply a loading dose. Once the gel transforms into a more viscous material phase, the drug release rate slows down to a more controlled rate. This dual phase release pattern is, in fact, highly desirable in practice for the treatment of microbial infection. The receptor fluids of each of the test vials are exchanged with the same volume of fluid every day for at least five days for the purpose of this experiment.

Results of such experiments show that the drug is released from such fluid viscous gel compositions in a sustained manner.

Quantity of the drug released from the respective compositions can be varied by manipulating factors such as solubility of drug by proper selection of its salt or ester, drug loading in the composition, molecular weight of the copolymer or adding other polymer. For example, compositions of the present invention containing tetracycline hydrochloride salt would release this drug at a faster rate compared to the release of tetracycline base from compositions of the present invention. This is believed to be due to the fact that the hydrochloride salt of tetracycline is about six times more soluble than the tetracycline base.

Such experiments demonstrate that sustained release fluid viscous gel or paste compositions of poly(lactyl-co-glycolide) can be formulated using triacetin according to this invention without using any objectionable organic solvents such as acetone or methylene chloride for delivery of the drugs into the body cavities.

What is claimed is:

1. A fluid viscous syringable gel or paste composition consisting essentially of:
   (a) about 1% to about 90% of triacetin as as essential non-toxic carrier and stabilizer;
   (b) about 1% to about 90% of a copolymer of from about 15% to about 85% each of lactide and glycolide monomers and having a molecular weight of about 1,000 to about 120,000 stabilized by said triacetin; and (c) about 1% to about 90% of a drug active agent; and wherein further said composition is in the form of a fluid viscous gel or paste suitable for being syringed into or around a periodontal pocket.

2. A composition according to claim 1 wherein the concentration of the drug active is from about 10% to about 50% and the active is selected from the tetracycline group is antibiotics.

3. A method of treating diseases of the oral cavity in a human or lower animal suffering from such disease by placing into the periodontal pocket or around said pocket of said human or lower animal a composition according to claim 1.

4. A method according to claim 3 wherein the drug active is selected from the tetracycline group of antibiotics.

5. A method according to claim 4 wherein the composition is a gel suitable for insertion into or around the periodontal pocket and whereby said gel is inserted into or around the periodontal pocket by using a syringe-like apparatus.

* * * * *

UNITED STATES PATENT OFFICE
CERTIFICATE OF CORRECTION

PATENT NO. : 5,242,910
DATED : September 7, 1993
INVENTOR(S) : Nalinkant C. Damani It is certified that error appears in the above-identified patent and that said Letters Patent is hereby corrected as shown below:

On the title page,
In the heading, inventor name "DAMANJ" should be --DAMANI--.

[75] Inventor "Damanj" should be --Damani--.

Signed and Sealed this

Twelfth Day of April, 1994

Attest:

BRUCE LEHMAN

Attesting Officer     Commissioner of Patents and Trademarks